United States Patent [19]
Kissinger

[11] Patent Number: 5,185,475
[45] Date of Patent: Feb. 9, 1993

[54] PROCESS FOR PREPARING PARACUMYLPHENOL

[75] Inventor: Gaylord M. Kissinger, Evansville, Ind.

[73] Assignee: General Electric Company, Mt. Vernon, Ind.

[21] Appl. No.: 891,025

[22] Filed: Jun. 1, 1992

[51] Int. Cl.$^5$ .................... C07C 37/14; C07C 39/14
[52] U.S. Cl. .................... 568/748; 568/744; 568/747
[58] Field of Search ............ 568/724, 744, 747, 748

[56] References Cited

U.S. PATENT DOCUMENTS 2,882,322  8/1959  Griffin et al. .................... 568/744
4,906,791  3/1990  Imanari et al. .................... 568/744

FOREIGN PATENT DOCUMENTS 0188535  11/1982  Japan .................... 568/744

OTHER PUBLICATIONS

Chem. Abstracts 91:157444z, High Purity Stabilized P-Cumylphenol, Zieborak et al., Pol 100,643, Feb. 15, 1979, Application 194205, Jul. 12, 1976.

*Primary Examiner*—Werren B. Lone
*Attorney, Agent, or Firm*—Martin Barancik

[57] ABSTRACT

A method for preparing paracumylphenol in a highly selective manner which comprises
  a. reacting alpha methylstyrene with a purity greater than about 99.5 wt. % with a molecular excess of phenol having a purity greater than about 99.95 wt. % in the contact presence of a solid organic cation exchange resin at a temperature of from about 40° C. to about 100° C. and obtaining a stream containing paracumylphenol, phenol and small quantitities of side reaction products comprising orthocumylphenol and alpha methylstyrene dimers,
  b. removing excess phenol and other unwanted materials which are lower boiling than paracumylphenol, thereby leaving a stream which is at least about 99 wt. % paracumylphenol.

8 Claims, No Drawings

PROCESS FOR PREPARING PARACUMYLPHENOL

BACKGROUND OF THE INVENTION

Paracumylphenol has many uses including the preparation of disinfectants, ionic sufactants, anti-oxidants and resins. However, one of the chief obstacles that has appeared to limit its usage in these areas is its relatively high cost of preparation. Although many processes have been used to prepare paracumylphenol, the underlying price is still relatively high. Recently, substantial focus has been directed at utilizing the side and waste streams of the process for preparing phenol from cumene. However the actual process steps of purifying the paracumylphenol which is present as a side product in the phenol process has also made these particular efforts less economical. Therefore a simple, inexpensive process for preparing paracumylphenol is in demand.

A new process for preparing paracumylphenol has been developed. This process is simple, inexpensive, highly selective, and does not require any purge streams, free acid recovery, solvent recovery, rotating machinery for product recovery, waste stream treatment, product drying, and other steps.

SUMMARY OF THE INVENTION

A method for preparing paracumylphenol in a highly selective manner which comprises
 a. reacting alpha methylstyrene with a purity greater than about 99.0 wt. % with a molecular excess of phenol having a purity greater than about 99.90 wt. % in the contact presence of a solid organic cation exchange resin at a temperature of from about 40° C. to about 100° C. and obtaining a stream containing paracumyl phenol, phenol and small quantities of side reaction products comprising orthocumylphenol and alpha methylstyrene dimers,
 b. removing excess phenol and other unwanted materials which are lower boiling than paracumylphenol, thereby leaving a stream which is at least about 98 wt. % paracumylphenol.

DETAILED DESCRIPTION OF THE INVENTION

The alpha methylstyrene employed should have a weight percent purity above about 99.0 wt. %, preferably above about 99.5 wt. %. The phenol employed as the reactant should be above about 99.90 wt. % purity and preferably above about 99.95 wt. % purity. Such alpha methylstyrene and phenol are readily obtained as a side product and the main product from a process starting from cumene. The phenol can be the direct product of such process or obtained from market sources and the alpha methylstyrene can be obtained from market sources. The alpha methylstyrene and phenol are contacted in quantitites wherein there is a substantial excess of phenol. Generally an excess as measured in moles of from about 3 times to about 15 times excess phenol to AMS can be employed. These streams are passed over an acid catalyst system. Although any acid catalyst system can be employed it is much preferred to employ a solid acid catalyst system so that there are no unnecessasy separation steps of one liquid from another or acid recovery steps. Such acid catalyst systems are commonly present as organic acid catalyst systems such as the sulfonic acid cation exchange resins manufactured by various companies. Examples of acidic ion exchange resins useful in catalyzing this reaction are generally well known compositions as are methods of their preparation, see for example the preparative procedures described in U.S. Pat. No. 3,037,052 which is hereby incorporated herein by reference thereto. Representative of acid ion-exchange resins are strong-acid ion exchangers, such as those resins or polymers having a plurality of pendant sulfonic acid groups. Examples include sulfonated polystyrene or poly(styrenedivinylbenzene) copolymer and sulfonated phenolformaldehyde resins. The sulfonated resins are commercially available in water swollen form as gellular and macro-reticular types. Specific examples of commercially available resins are Amberlite IR-120H, Amberlyst 15H, Amberlyst 31, Dowex 50-X-4, Dowex MSC-lH, Duolite c-(Amberlite, Amberlyst, Dowex, Duolite, Permutit, Chempro and Imac are registered U.S. Trademarks). Further examples of such ion exchangers as well as methods for preparing such ion exchangers are described in the Encyclopedia of Polymer Science and Technology, 1967, vol. 7, pages 695 to 708 and third edition, 1981. The exchange capacity of the acidic resin is preferably at least 2.0 meq. H+/g of dry resin, with exchange capacities in the range of from 3.0 to 5.5 meg. H+/g (dry resin) particularly preferred. One preferred catalyst is the Amberlyst ® gelular types, which are styrene cross-linked with divinlybenzene or like cross-linking monomer and having pendant sulfonic acid groups attached to the aromatic nucleus of the styrene moiety. Sulfonation may be by the process described in U.S. Pat. No. 2,366,007 which is incorporated herein by reference thereto.

Preferred catalyst systems include a cation exchange resin such as Rohm and Haas XE-364. This resin is a sulfonated polystyrene. Either a single reactor or multiple reactors in series can be used. However the feed rate as measured in weighted hourly space velocity (whsv) can vary between from about 0.1 to 10.0 pounds feed/hr. per pound dry catalyst. Preferred is about 0.2 to 6.0. Of course, the feed rate determines the residence time of the feed materials in contact with the catalyst and therefore helps to determine the conversion and selectivity in the actual reaction. Usually most reactions are a compromise between conversion and selectivity. The longer the residence time the greater the conversion; however, the lower the selectivity. Temperatures of the reactor are from about 40 to about 100° C., again having the expected impact on productivity and selectivity of the reaction step.

Generally the exiting stream from the reactor or series of reactors has had 100% of the AMS converted to a product. This product is very rich in paracumylphenol. There is a small amount of orthocumylphenol, dimers of AMS and other usually unknown side products. This stream is then preferably contacted with a material which is anionic and which neutralizes or renders ineffective for catalyzing any future side reactions materials from the cation exchange resin which are leached out or removed by the stream contacting the catalyst. Such anionic materials can be weak basic or weak salts which can bring about the neutralization of any material leached from the catalyst such as oligomers bearing the cationic group. Examples of such weak bases include the carbonates such as barium carbonate, magnesium carbonate and manganese carbonate. However because of the potential separation problems present with such materials it is better to use a solid anion exchange resin to bring about such effect.

The ion exchange resins useful in the method of this invention include all known basic resins of this type. For the most part, they are amine or quaternary ammonium resins typically containing such moieties as dimethylbenzylamino groups or corresponding methylquaternized groups attached to a polymer chain. Amine resins including those having a pyridyl group are often preferred. For the purpose of the invention, the amine resins are employed in the free base form, although quaternary resins wherein the counterion therein is a hydroxide anion can also be used.

Methods of preparing anionic exchange resins are generally well known; see for example the method described in U.S. Pat. No. 2,632,001 (McMasters et al.) incorporated herein by reference thereto. This method comprises the side-chain chlorination of poly(vinyltoluene), followed by reaction with a tertiary amine in the presence of a polar solvent such as water to form a quaternary ammonium salt. Representative of commercially available resins of this type are Amberlite IRA-400, Amberlite IRA-401, Amberlite IRA-402, Amberlite IRA-900, Duolite A-101-D, Duolite ES-111, Dowex 1, Dowex 11, Dowex 21K, and Ionac A-540 and those derived from dimethylethanolamine$(CH_3)_2$-$NCH_2CH_2$ OH, Amberlite IRA-410, Amberlite IRA-911, Dowex 2, Duolite A-102-D, Ionac A-542, and Ionac A-550 (Amberlite, Duolite, Dowex and Ionac are registered U.S. trademarks).

Preferred for use in the present invention are weakbase anionic exchange resins, containing primary, secondary and tertiary amine groups. Commercially available examples of these products are Amberlite A-21, Dowex 44, Duolite A-7, Ionac A-260, Amberlite IRA-35, Amberlite IRA-68 (the latter two resins are gelular with acrylic backbones) and Reillex-402, a polyvinyl pyridine from. Reilly Industries, Inc.

Contact between the paracumylphenol stream in the anion exchange resin may be affected by any convenient means. Generally, the stream passes through the resin at temperatures in a range which is similar to that wherein the conversion of the phenol to the paracumylphenol occurs. Generally such temperature is from about 40° to about 120° C. preferably from about 50° to 75° C. Passage of the phenol mixture through the resin may be upward or downward, for time sufficient to remove any contaminants which may be present. As in the acidic cation exchange resin utilized in the first step, such anion exchange resin may be used until it has been exhausted. Standard regeneration procedures my be used for either the cation exchange or the anion exchange resins employed in this process.

As noted before there is a substantial amount of excess phenol present in the reaction. All of this phenol has been carried along through the past processing. This excess phenol is now removed. The phenol can be removed by standard processing such as distillation since its boiling point is significantly different than the paracumylphenol and many other side products and impurities present. Generally such separation occurs in a stripping type reaction at a reduced pressure and a relatively low temperature utilizing standard operational apparatuses. A further removal can be made by utilizing a desorbtion process in the presence of a non reactive gas and surface enhancer such as packing in a column. Examples of such a gas are nitrogen and carbon dioxide, preferably nitrogen. The phenol is removed in a relatively gentle process from the desired paracumylphenol at a reduced . pressure and a relatively low temperature. Depending upon the yields required as well as the purity as measured by weight percent and the quality of the desired paracumylphenol as measured for example by color, all of these procedures can be used to remove various percentages of the phenol or only one procedure can be employed.

Generally, an appropriate balance of the processing conditions can bring about at least 97 to 98 wt. % pure paracumylphenol with low amounts of AMS dimers, orthocumylphenol and other materials. The precise composition analysis will vary depending upon the particular operating conditions. Generally the product has an APHA color of 5 or less units in a 10% paracumylphenol in methanol solution. However all of these quantities can vary somewhat dependent upon the conditions of reaction in the phenol removal. The product can be collected by flaking or prilling the melt or, if desired, even further purification steps can be done such as passing the melt to a falling film melt crystallizer. In fact the actual material need not be solidified but can be used in its melt form. For example paracumylphenol is a known endcapper for resins wherever another phenol such as normal phenol can be employed. Such endcapper can be used in the preparation of polycarbonate, polyestercarbonate, polyarylate, and other resins. The paracumylphenol endcapping agent can therefore be passed in the melt or if desired flaked or prilled and added as a solid or as a salt to a reactor preparing aromatic polycarbonate from a dihydric phenol and a carbonate precursor such as phosgene in the standard interfacial reaction. Such reaction includes dihydric phenols such as bisphenol-A and an alkaline solution such as sodium hydroxide together with an organic solvent in which the resin will be soluble such as methylene chloride. The paracumylphenol endcapping agent can be added in the melt or added as a solid to the sodium hydroxide and then added directly to the formulation mixture or the reactor. Phosgene is then pumped into the reactor together with an interfacial catalyst system such as amine for example triethylamine or 2-ethyl pyridine and the reaction allowed to go to completion. These are standard reaction conditions and appear in numerous patents for the preparation of polycarbonate. A further method of preparing polycarbonate is the melt reaction wherein a dihydric phenol in its melt form together with a carbonate precursor such as diphenyl carbonate also in its melt form are contacted without the presence of a solvent but with a transesterification catalyst system together with an endcapping agent such as the paracumylphenol and heated to a temperature wherein the transesterification reaction proceeds thereby making aromatic polycarbonate resin. Examples of such melt methods for making aromatic polycarbonates are present in the patent literature.

It is further noted that the color of the product paracumylphenol can be significantly improved by the addition of certain additives for example hypophosphorous acid. Such addition can occur anywhere in the actual process and in fact can be used to a particular advantage when the paracumylphenol melt need be held in storage. The actual addition point in the process can be in the streams contacting the cation exchange resin, however it is preferred to add such color stabilizing additive after the contacting of the product stream with the anionic material, when it is employed.

For process economics it is quite clear that the phenol which has been removed can be recycled to the reactor. It should also be noted that isomers of paracumylphenol which traveled together with the removed phenol can also be present and contact the cation exchange catalyst once more in the presence of new phenol and AMS. Such cation exchange resin has the ability to rearrange certain byproducts to the desired paracumylphenol.

Below are specific examples of the invention. They are present to illustrate the invention and are not there to unduly limit the general scope of the invention.

EXAMPLE 1

70 grams of a dried Lewatit sulfonated polystyrene cation exchange resin was charged to a jacketed glass cylinder. Phenol having a weight percent purity of 99.95% was mixed with alphamethyl styrene of 99.7 wt. % purity in proportions of 10.4 to 1 mole ratio phenol to AMS. This stream was pumped through the cationic bed at a WHSV of 1.55 pounds feed/hour per pound dry catalyst. Also present in the jacketed glass cylinder downstream was 10 grams of dried anionic resin, Rohm and Haas A-21. Therefore after leaving the cation exchange resin the stream now having the paracumylphenol therein contacted the anion exchange resin. This stream is now introduced into a device for removing excess phenol, and a portion of the by-products. This can be accomplished by passing the stream through a packed column, with inert gas, such as $N_2$, passing through the packed bed to strip off the phenol and other by-products which are more volatile than paracumylphenol. A vacuum stripper column can also be used to provide an efficient low temperature phenol removal step, followed by inert gas stripping to remove the last traces of phenol. The p-cumylphenol, at a purity of 98.2% + 1.4% o-cumyulphenol was recovered from the melt as flakes, formed on a cool surface.

EXAMPLE 2

Phenol was pumped at a rate of 1.1 ml/min, at about 50° C., into a mixer, where 99.5% pure AMS was mixed at a rate of 0.12 ml/min. This combined stream of 1.22 ml/min, at about 50° C., was pumped into 70g dry Rohm and Haas XE-364 sulfonated polystyrene cationic exchange resin. The flow direction was downward, and the reactor was held at about 60° C. After the reactor effluent stream passed through the cationic resin, it was passed through 10g of A-21 anionic resin.

The effluent stream at 1.22 ml/min, after passing the cationic and anionic exchange resins was fed to the top of a column containing about 200cc of packing material, consisting of 4mm diameter spherical glass beads. The aspect ratio of this column is about 20:1, that is, 1" diameter × 20" height. This column was jacketed with hot oil at a temperature held typically at 140° C. Nitrogen was passed upward through the column at a rate of about 20 SCFH (20 std. cubic feet/hour) which is equivalent to about 60 SCFM/square foot cross sectional area of packing.

The overhead vapors from this column were separated from the nitrogen gas flow by passing through water cooled condensers, forming liquid condensate, and allowing the nitrogen to pass through to atmosphere. This liquid condensate which had a typical composition of about 96% phenol, 3% paracumylphenol, 0.5% orthocumylphenol, 0.3% AMS dimers and 0.2% "others". This overhead condensate was recycled 100% to the cationic reactor.

The PCP at the bottom of the column, having a typical composition of 98.2% PCP, 1.4% OCP, 0.16% AMS dimers, 0.24% others, was solidified from the melt as flakes.

EXAMPLE 3

Recycle phenol was pumped at 0.5 GPM and mixed with alphamethyl styrene at 0.055 GPM through a reactor bed (XE-364 Rohm & Haas) containing about 178 dry pounds of resin, WHSV = 1.6.

The reactor effluent (4) was fed to a phenol stripper. The stripper overhead condensate (5) was recycled to a recycle feed tank. The bottoms of the stripper was fed to a desorber. The desorber overhead condensate was recycled to the recycle feed tank. The bottoms was recovered on a flaker.

The bottoms showed paracumylphenol being formed at the rate of 39.0 lb./hr. together with 0.54 lb./hr. of orthocumylphenol, 0.06 lbs./hr. of AMS dimers and 0.09 lbs. /hr. of others.

What is claimed is:

1. A method for preparing paracumylphenol in a highly selective manner which comprises
    a. reacting alpha methylstyrene with a purity greater than about 99.5 wt. % with a molecular excess of phenol having a purity greater than about 99.95 wt. % in the contact presence of a solid organic cation exchange resin at a temperature of from about 40° C. to about 100° C. and obtaining a stream containing paracumylphenol, phenol and small quantities of side reaction products comprising orthocumylphenol and alpha methylstyrene dimers,
    b. removing excess phenol and other unwanted materials which are lower boiling than paracumylphenol, thereby leaving a stream which is at least about 98 wt. % paracumylphenol.

2. The method in accordance with claim 1 wherein prior to removing excess phenol of step b, the said stream prepared in step a is contacted with an anion so as to neutralize cation which may be present.

3. The method in accordance with claim 1 wherein hypophosphorous acid is present with the paracumylphenol.

4. The method in accordance with claim 1 wherein the paracumylphenol prepared is utilized as a chain stopping agent in the preparation of aromatic polycarbonate.

5. The method in accordance with claim 4 wherein the aromatic polycarbonate is bisphenol-A polycarbonate.

6. The method in accordance with claim 3 wherein the hypophosphorous acid is added after the cation exchange resin.

7. The method in accordance with claim 2 wherein the anion is in the form of a solid anion exchange resin.

8. The method in accordance with claim 7 wherein the hypophosphorous acid is added after the anion exchange resin bed.

* * * * *